United States Patent
Moe

(10) Patent No.: US 9,820,825 B2
(45) Date of Patent: *Nov. 21, 2017

(54) SURGICAL SYSTEM HAVING PLURALITY OF DETACHABLY ATTACHABLE COMPONENTS AND CIRCUIT FOR DETECTING TARGET STATES OF DETACHABLY ATTACHABLE COMPONENTS AND PERFORMING CONTROL BASED ON DETECTED TARGET STATES, AND METHOD FOR PROVIDING SURGICAL SYSTEM

(71) Applicant: GYRUS ACMI INC., Southborough, MA (US)

(72) Inventor: Riyad Moe, Madison, WI (US)

(73) Assignee: GYRUS ACMI INC., Southborough, MA (US)

( * ) Notice: Subject to any disclaimer, the term of this patent is extended or adjusted under 35 U.S.C. 154(b) by 240 days.

This patent is subject to a terminal disclaimer.

(21) Appl. No.: 14/627,103

(22) Filed: Feb. 20, 2015

(65) Prior Publication Data
US 2016/0242850 A1    Aug. 25, 2016

(51) Int. Cl.
| | |
|---|---|
| *A61B 90/90* | (2016.01) |
| *A61B 18/14* | (2006.01) |
| *A61B 17/00* | (2006.01) |
| *A61B 90/98* | (2016.01) |

(52) U.S. Cl.
CPC ............ *A61B 90/90* (2016.02); *A61B 18/14* (2013.01); *A61B 90/98* (2016.02); *A61B 2017/00199* (2013.01); *A61B 2017/00225* (2013.01); *A61B 2017/00482* (2013.01)

(58) Field of Classification Search
CPC .......... A61B 2017/00199; A61B 2017/00225; A61B 2018/00642; A61B 90/90; A61B 90/98
See application file for complete search history.

(56) References Cited

U.S. PATENT DOCUMENTS

| | | |
|---|---|---|
| 3,223,088 A | 12/1965 | Barber et al. |
| 3,955,284 A | 5/1976 | Balson |
| 4,014,342 A | 3/1977 | Staub et al. |
| 4,878,493 A | 11/1989 | Pasternak et al. |
| 5,112,299 A | 5/1992 | Pascaloff |
| 5,230,704 A | 7/1993 | Moberg et al. |

(Continued)

FOREIGN PATENT DOCUMENTS

| | | |
|---|---|---|
| EP | 1 201 196 A1 | 5/2002 |
| EP | 2 044 893 A2 | 4/2009 |

(Continued)

OTHER PUBLICATIONS

International Search Report and Written Opinion dated Mar. 25, 2014 from International Application No. PCT/US2013/077758.

*Primary Examiner* — Eric D. Bertram
(74) *Attorney, Agent, or Firm* — Scully, Scott, Murphy & Presser, P.C.

(57) ABSTRACT

Techniques, including a surgical system and a method for providing a surgical system, for detecting detachable attachment of a first component to a console, for detecting detachable attachment of a second component to one of the console the first component, and for controlling a function module based on the detection result are provided.

16 Claims, 11 Drawing Sheets

(56) References Cited

U.S. PATENT DOCUMENTS

| | | | |
|---|---|---|---|
| 5,275,609 A | 1/1994 | Pingleton et al. | |
| 5,352,222 A | 10/1994 | Rydell | |
| 5,376,078 A | 12/1994 | Dinger, III et al. | |
| 5,383,874 A * | 1/1995 | Jackson | A61B 18/00 606/1 |
| 5,395,312 A | 3/1995 | Desai | |
| 5,405,348 A | 4/1995 | Anspach, Jr. et al. | |
| 5,413,556 A | 5/1995 | Whittingham | |
| 5,492,527 A | 2/1996 | Glowa et al. | |
| 5,540,708 A | 7/1996 | Lim et al. | |
| 5,560,373 A | 10/1996 | DeSantis | |
| 5,569,254 A | 10/1996 | Carlson et al. | |
| 5,609,573 A | 3/1997 | Sandock | |
| 5,620,415 A | 4/1997 | Lucey et al. | |
| 5,620,447 A | 4/1997 | Smith et al. | |
| 5,647,869 A | 7/1997 | Goble et al. | |
| 5,712,543 A | 1/1998 | Sjostrom | |
| 5,792,167 A | 8/1998 | Kablik et al. | |
| 5,810,809 A | 9/1998 | Rydell | |
| 5,814,044 A | 9/1998 | Hooven | |
| 5,849,023 A | 12/1998 | Mericle | |
| 5,873,886 A | 2/1999 | Larsen et al. | |
| 5,899,915 A | 5/1999 | Saadat | |
| 5,904,681 A | 5/1999 | West, Jr. | |
| 6,042,593 A | 3/2000 | Storz et al. | |
| 6,053,923 A | 4/2000 | Veca et al. | |
| 6,074,386 A * | 6/2000 | Goble | A61B 18/1206 606/34 |
| 6,152,941 A | 11/2000 | Himes et al. | |
| 6,217,598 B1 | 4/2001 | Berman et al. | |
| 6,221,088 B1 | 4/2001 | Bays | |
| 6,246,638 B1 | 6/2001 | Zook et al. | |
| 6,293,957 B1 | 9/2001 | Peters et al. | |
| 6,296,638 B1 | 10/2001 | Davison et al. | |
| 6,454,782 B1 | 9/2002 | Schwemberger | |
| 6,494,892 B1 | 12/2002 | Ireland et al. | |
| 6,652,514 B2 | 11/2003 | Ellman et al. | |
| 6,716,215 B1 | 4/2004 | David et al. | |
| 6,752,816 B2 | 6/2004 | Culp et al. | |
| 6,824,550 B1 | 11/2004 | Noriega et al. | |
| 6,979,332 B2 | 12/2005 | Adams | |
| 7,237,990 B2 | 7/2007 | Deng | |
| 7,247,161 B2 | 7/2007 | Johnston et al. | |
| 7,416,539 B2 | 8/2008 | Johnston et al. | |
| 7,674,263 B2 | 3/2010 | Ryan | |
| 9,387,050 B2 * | 7/2016 | Church | A61B 18/1206 |
| 2003/0165794 A1 * | 9/2003 | Matoba | A61C 1/0007 433/114 |
| 2004/0010258 A1 | 1/2004 | Carusillo et al. | |
| 2004/0147947 A1 * | 7/2004 | Donofrio | A61B 17/320068 606/169 |
| 2004/0167427 A1 | 8/2004 | Quick et al. | |
| 2009/0275940 A1 * | 11/2009 | Malackowski | A61B 18/1442 606/42 |
| 2010/0317998 A1 | 12/2010 | Hibner et al. | |
| 2011/0017801 A1 | 1/2011 | Zemlok et al. | |
| 2011/0066142 A1 | 3/2011 | Tal et al. | |
| 2014/0155888 A1 * | 6/2014 | Edwards | A61B 18/1482 606/42 |

FOREIGN PATENT DOCUMENTS

| | | |
|---|---|---|
| EP | 2 133 028 A2 | 12/2009 |
| GB | 2470607 A | 12/2010 |

\* cited by examiner

FIG. 3
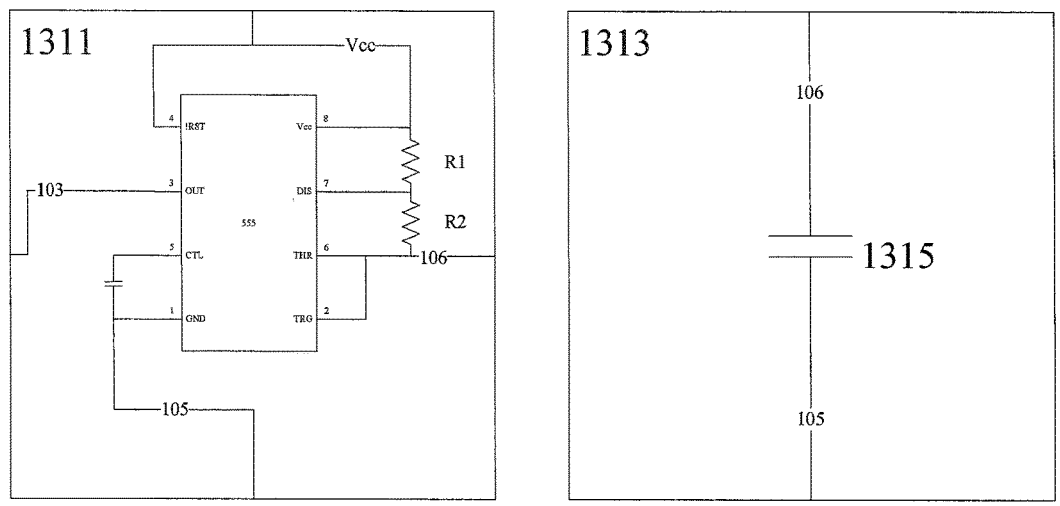
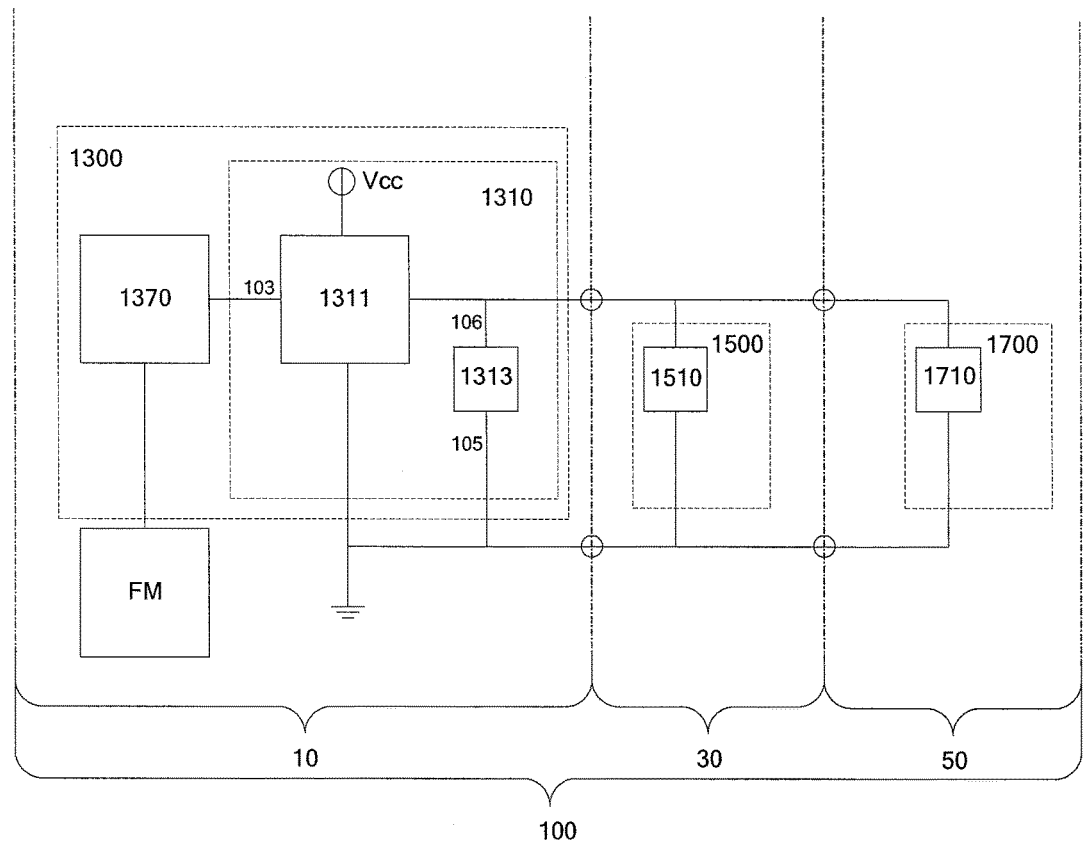

FIG. 4
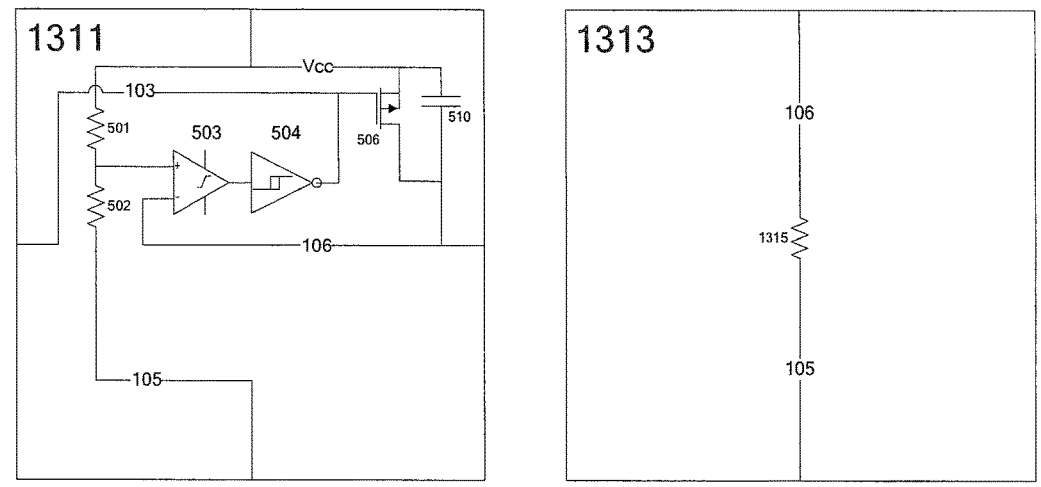
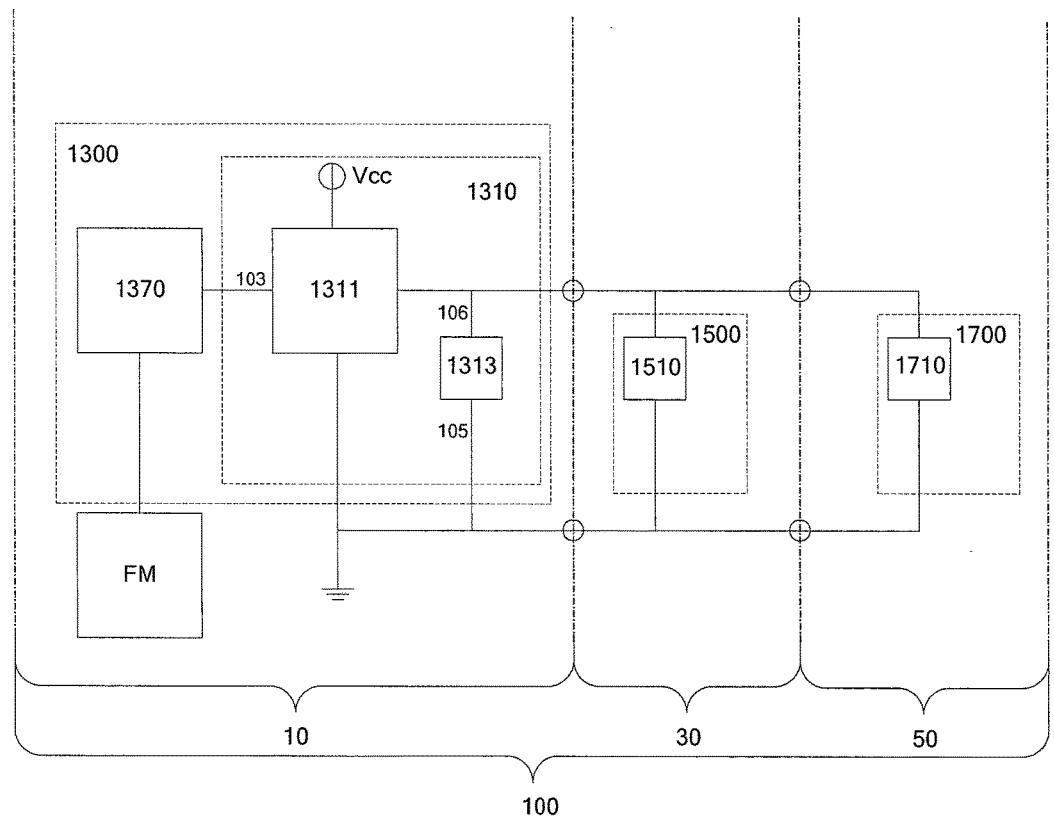

FIG. 5
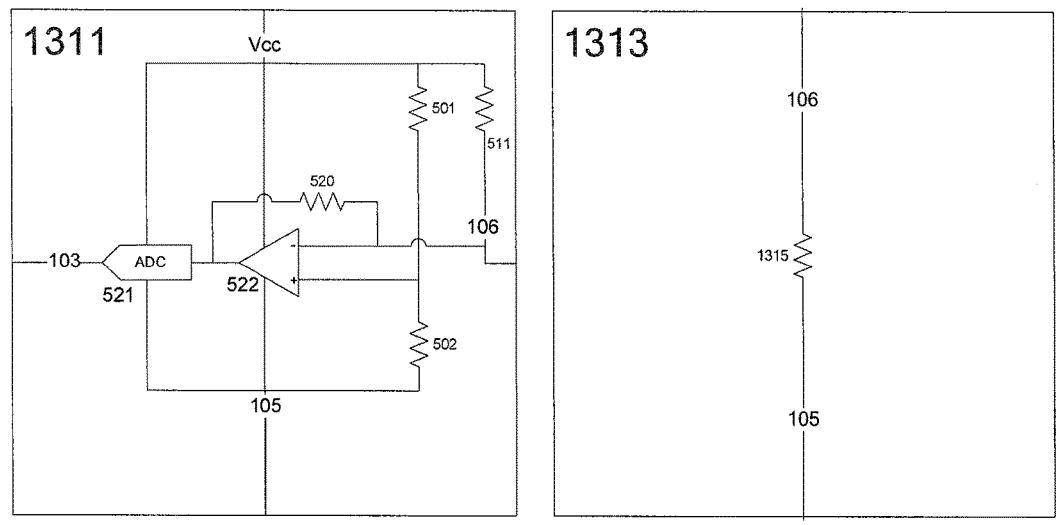
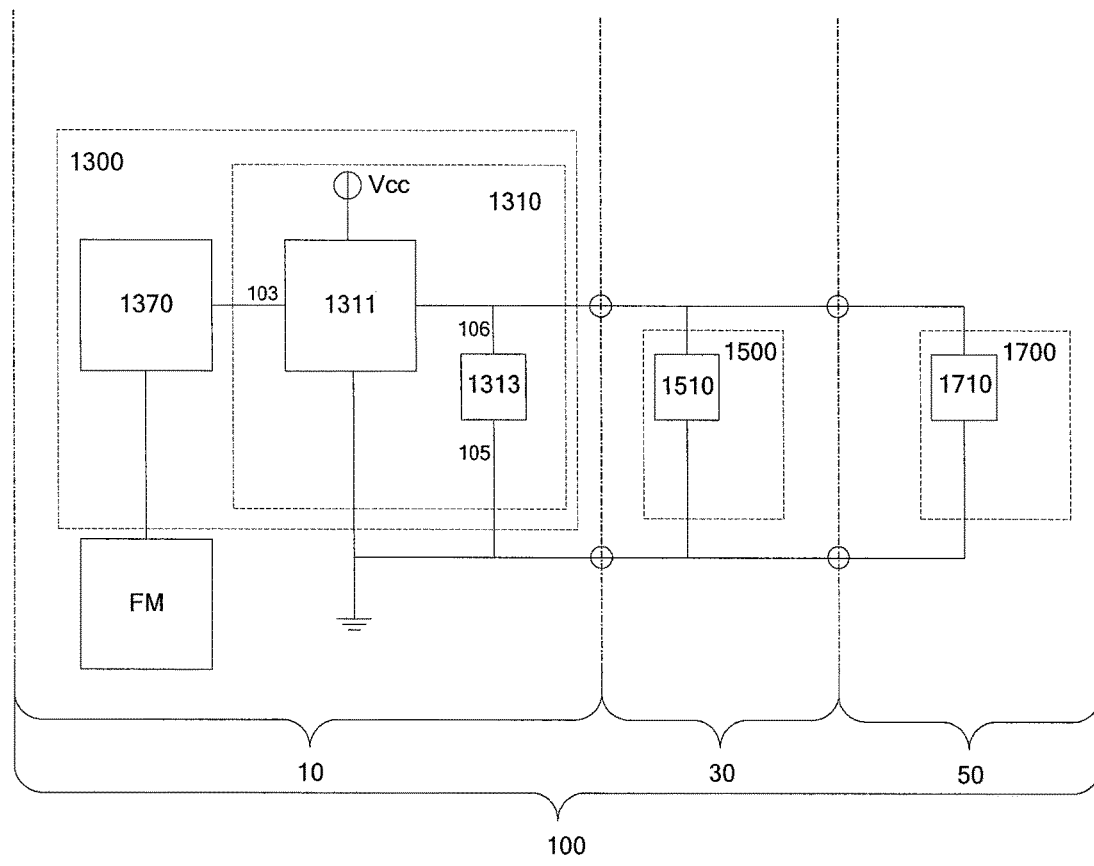

SURGICAL SYSTEM HAVING PLURALITY OF DETACHABLY ATTACHABLE COMPONENTS AND CIRCUIT FOR DETECTING TARGET STATES OF DETACHABLY ATTACHABLE COMPONENTS AND PERFORMING CONTROL BASED ON DETECTED TARGET STATES, AND METHOD FOR PROVIDING SURGICAL SYSTEM

BACKGROUND

The invention relates generally to a console and a plurality of detachably attachable components that are directly or indirectly attached to the console, a surgical system including the console, a surgical system including the console and the plurality of detachably attachable components, and a method of providing the surgical system.

The invention further relates to techniques for detecting a plurality of target states of the plurality of detachably attachable components and control of one or more functions based on the detected plurality of target states.

SUMMARY

In accordance with a first embodiment, a surgical system is provided. The surgical system comprises: a console comprising: a function module configured to be controlled to perform a predetermined function; and a controller configured to control the function module; a first component configured to be directly or indirectly detachably attached to the console; a second component configured to be directly or indirectly detachably attached to one of the console and the first component, a target state detection circuit arranged to the console, the target state detection circuit comprising: a detection signal generation circuit configured to generate a detection signal; and a reference circuit configured to provide a baseline signal based on the detection signal; a first target state identification circuit arranged to the first component, wherein the first target state identification circuit is configured to be selectively electrically connected in a first attached state to the target state detection circuit, and wherein in the first attached state, the target state detection circuit and the first target state identification circuit are configured to provide a first attachment state signal based on the detection signal; and a second target state identification circuit arranged to the second component, wherein the second target state identification circuit is configured to be selectively electrically connected in a second attached state to the target state detection circuit, and wherein in the second attached state, the target state detection circuit and the second target state identification circuit are configured to provide a second attachment state signal based on the detection signal, wherein the target state detection circuit is configured to output a feedback signal based on the baseline signal, the first attachment state signal, and the second attachment state signal, and wherein the controller is configured to control the function module based on the feedback signal.

In accordance with a second embodiment, a surgical system is provided. The surgical system comprises: a console comprising: a function module configured to be controlled to perform a predetermined function; and a controller configured to control the function module, wherein the console is configured to be directly or indirectly detachably attached to a first component, and wherein one of the console and the first component is configured to be directly or indirectly detachably attached to a second component; and a target state detection circuit arranged to the console, the target state detection circuit comprising: a device signal generation circuit configured to generate a detection signal; and a reference circuit configured to provide a baseline signal based on the detection signal, wherein the target state detection circuit is configured to be selectively electrically connected in a first attached state to a first target state identification circuit arranged to the first component, wherein in the first attached state, the first target state identification circuit is configured to provide a first attachment state signal based on the detection signal, wherein the target state detection circuit is configured to be selectively electrically connected in a second attached state to a second target state identification circuit arranged to the second component, wherein in the second attached state, the second target state identification circuit is configured to provide a second attachment state signal based on the detection signal, and wherein the target state detection circuit is configured to output a feedback signal based on the baseline signal, the first attachment state signal, and the second attachment state signal, and wherein the controller is configured to control the therapy signal generator based on the feedback signal.

In accordance with a third embodiment, a method of providing a surgical system is provided. The method comprises: providing a console comprising: a function module configured to be controlled to perform a predetermined function; and a controller configured to control the function module; providing a first component configured to be directly or indirectly detachably attached to the console; providing a second component configured to be directly or indirectly detachably attached to one of the console and the first component, providing a target state detection circuit arranged to the console, the target state detection circuit comprising: a detection signal generation circuit configured to generate a detection signal; and a reference circuit configured to provide a baseline signal based on the detection signal; providing a first target state identification circuit arranged to the first component, wherein the first target state identification circuit is configured to be selectively electrically connected in a first attached state to the target state detection circuit, and wherein in the first attached state, the target state detection circuit and the first target state identification circuit are configured to provide a first attachment state signal based on the detection signal; providing a second target state identification circuit arranged to the second component, wherein the second target state identification circuit is configured to be selectively electrically connected in a second attached state to the target state detection circuit, and wherein in the second attached state, the target state detection circuit and the second target state identification circuit are configured to provide a second attachment state signal based on the detection signal; enabling the target state detection circuit to output a feedback signal based on the baseline signal, the first attachment state signal, and the second attachment state signal; and enabling the controller to control the function module based on the feedback signal.

BRIEF DESCRIPTION OF THE DRAWINGS

The following detailed description, given by way of example and not intended to limit the invention solely thereto, will best be appreciated in conjunction with the accompanying drawings, wherein like reference numerals denote like elements and parts, in which:

FIG. 3 shows a surgical system 1-3 according to a third embodiment of the present invention.

FIG. 4 shows a surgical system 1-4 according to a fourth embodiment of the present invention.

FIG. 5 shows a surgical system 1-5 according to a fifth embodiment of the present invention.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the present invention is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

FIRST EMBODIMENT

Figure 1:
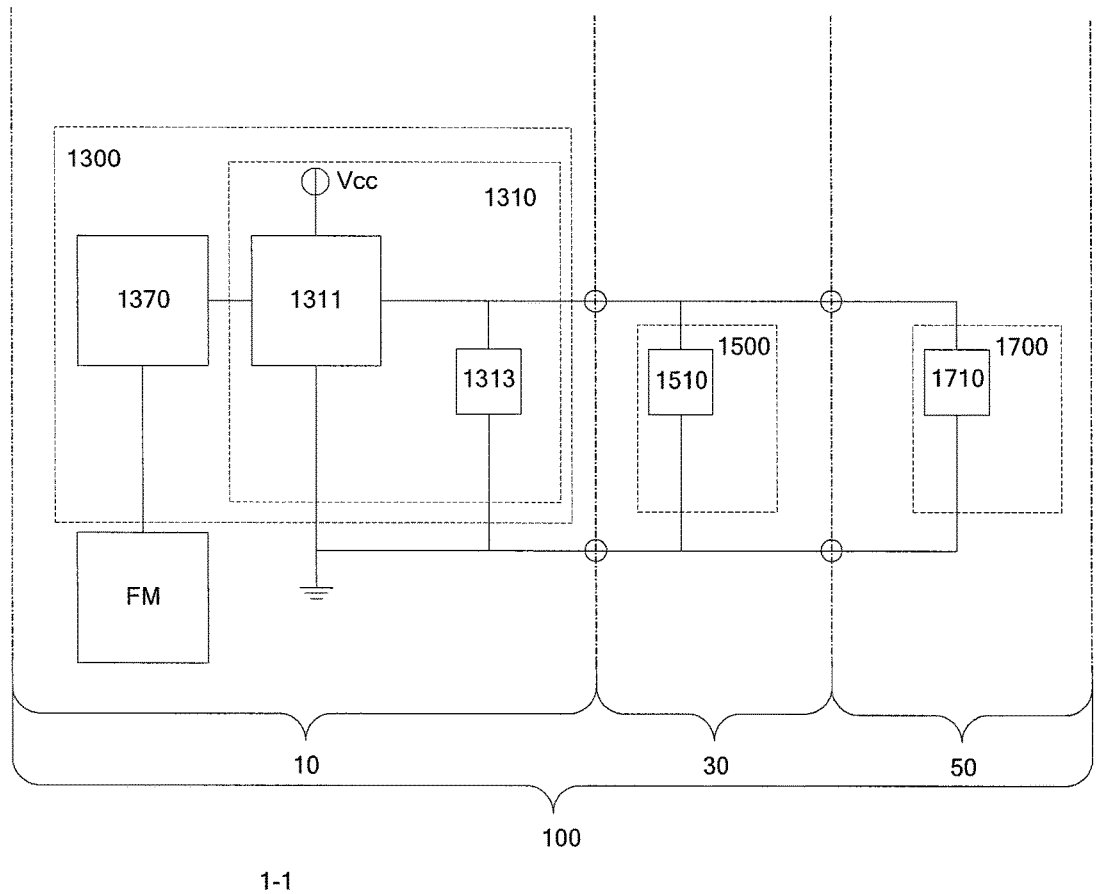
FIG. 1 shows a surgical system 1-1 according to a first embodiment of the present invention.

In a first embodiment, a surgical system 1-1 as shown in FIG. 1 is provided. The surgical system 1-1 includes a console 10, a first component 30 that is detachably attachable to the console 10, and a second component 50 that is detachably attachable to the first component 30.

The first component 30 and the second component 50 can be implemented as a debrider. An example of the first component 30 is a handpiece of the debrider. An example of the second component 50 is an interchangeable tip/blade module of the debrider that is detachably attachable to the handpiece. A description of a debrider including a handpiece and an interchangeable tip/blade module can be found in U.S. patent application Ser. No. 13/826,892, filed on Mar. 14, 2013 (now, U.S. Patent Application Publication No. 2014/0155923, published on Jun. 5, 2014), the content of which is incorporated herein by reference.

In the first embodiment and subsequently described embodiments, detachable attachment between two structures (e.g., detachable attachment between the first component 30 and the console 10, and detachable attachment between the second component 50 and the first component 30) can be implemented by one or more mechanical connections. Examples of mechanical connections that can be adapted to the embodiments described herein are described in, for example, U.S. Patent Application Publication Nos. US 2014/0005700 A1, US 2014/0155888 A1 and US 2014/0155889 A1. U.S. Patent Application Publication No. US 2014/0005700 A1 describes a surgical tool or blade retention assembly 40 at paragraphs [0030]-[0042] for selectively coupling and uncoupling (i.e, for detachably attaching) a surgical tool 20 (corresponding to the second component 50 described herein) to a handpiece (corresponding to the first component 30 described herein). The description of the surgical tool or blade retention assembly 40 described in U.S. Patent Application Publication No. US 2014/0005700 A1 is incorporated herein by reference. U.S. Patent Application Publication No. US 2014/0155889 A1 describes a handpiece provided with tip locking ports (that may be an aperture, a through hole, a dimple, or a combination thereof) and an interchangeable tip provided with connecting tabs that are sized to be accommodated in the tip locking ports to attach the interchangeable tip to the handpiece. The connecting tabs may be compressed to detach the interchangeable tip from the handpiece. The description of the tip locking ports and the connecting tabs in U.S. Patent Application Publication No. US 2014/0155889 A1 is incorporated herein by reference.

The surgical system 1-1 further includes a circuit 100 that is distributively arranged to the console 10, the first component 30, and the second component 50. The circuit 100 includes a function module FM for performing one or more functions (examples of which are described below), a target state control circuit 1300, a first target state identification circuit 1500, and a second target state identification circuit 1700. The function module FM and the target state control circuit 1300 are arranged in the console 10. The first target state identification circuit 1500 is arranged in the first component 30. The second target state identification circuit 1700 is arranged in the second component 50.

The target state control circuit 1300 includes a target state detection circuit 1310 configured to detect at least the following target states: a baseline attachment state in which the first component 30 is not attached to the console 10; a first attachment state in which the first component 30 is attached to the console 10 and the second component 50 is not attached to the first component 30; and a second attachment state in which the first component 30 is attached to the console 10 and the second component 50 is attached to the first component 30.

The target state detection circuit 1310 includes a detection signal generation circuit 1311 configured to provide a detection signal. The target state detection circuit 1310 further includes a reference circuit 1313 that is arranged to the console 10. The reference circuit 1313 is further arranged to be electrically connected to the detection signal generation circuit 1311.

In the baseline attachment state, the reference circuit 1313 is configured to output a baseline signal based on the detection signal, wherein the baseline signal indicates that the first component 30 is not attached to the console 10.

In the first attachment state, the reference circuit 1313 and the first target state identification circuit 1500 are electrically connected to the detection signal generation circuit 1311. Specifically, the first target state identification circuit 1500 is electrically connected to the detection signal generation circuit 1311 upon attachment of the first component 30 to the console 10. In an example, the console 10 and the first component 30 are provided with one or more pin and socket connectors to electrically connect the first target state identification circuit 1500 and the detection signal generation circuit 1311 upon attachment of the first component 30 to the console 10.

In the first attachment state, the reference circuit 1313 and the first target state identification circuit 1500 are configured to output a first attachment state signal based on the detection signal, wherein the first attachment state signal indicates that the first component 30 is attached to the console 10 and the second component 50 is not attached to the first component 30.

In the second attachment state, the reference circuit 1313, the first target state identification circuit 1500, and the second target state identification circuit 1700 are electrically connected to the detection signal generation circuit 1311 upon attachment of the first component 30 to the console 10 and attachment of the second component 50 to the first component 30. In an example, the first component 30 and the second component 50 are provided with one or more pin and socket connectors to electrically connect the second target state identification circuit 1700 to the detection signal generation circuit 1311 upon attachment of the second component 50 to the first component 30.

In the second attachment state, the reference circuit 1313, the first target state identification circuit 1500, and the second target state identification circuit 1700 are configured to output a second attachment state signal based on the detection signal, wherein the second attachment state signal indicates that the first component 30 is attached to the console 10 and the second component 50 is attached to the first component 30.

The target state control circuit 1300 further includes a controller circuit 1370 that can be implemented by hardware or a combination of hardware and software. The controller circuit 1370 is configured to control the function module FM based on the target state detected by the target state detection circuit 1310. Specifically, the controller circuit 1370 is configured to control the function module FM based on one or more of the baseline signal, the first attachment state signal, and the second attachment state signal.

In the first embodiment, the surgical system 1-1 is not limited to a single function module FM. The surgical system 1-1 can include a plurality of function modules. In such an implementation, the controller circuit 1370 is configured control one or more of the function modules based on one or more of the baseline signal, the first attachment state signal, and the second attachment state signal.

In the first embodiment, the surgical system 1-1 is not limited to two components that are detachably attachable in series to the console 10, and two target state identification circuits. The surgical system 1-1 can include n components (where n is an integer equal to or greater than 3), and a corresponding number of target state identification circuits arranged to the n components. The first component 30, the second component 50, and the n components can be attached in series to the console 10. In such an implementation, n attachment states can be detected by the target state control circuit 1300 and the controller circuit 1370 can control one or more function modules based on the detected attachment states.

In the first embodiment (and also in the subsequently described embodiments), the surgical system 1-1 is not limited to a single species of the first component 30, and is not limited to a single species of the second component 50. The surgical system 1-1 can also include two or more species of the first components 30, and two or more species of the second components 50.

Examples of two or more species of handpieces as two or more species of the first components 30, and examples of two or more species of tip/blade modules as two or more species of the second components 50 will be described below.

The surgical system 1-1 can include a debrider handpiece (having, for example, a pistol grip) as a first species of the first component 30 and a drill handpiece (having, for example, a pencil grip) as a second species of the first component 30.

The first species of the first component 30 is provided with a first species of the first target state identification circuit 1500 while the second species of the first component 30 is provided with a second species of the first target state identification circuit 1500 different from the first species of the first target state identification circuit 1500. The first and second species of the first target state identification circuit 1500 can be implemented by, for example, capacitors with different ratings. Based on this distinction, the target state detection circuit 1310 is able to detect from the first attachment state signal and the second attachment state signal the attachment of a handpiece to the console 10 and also the specific species of handpiece attached to the console 10.

The surgical system 1-1 can include a first tip module with monopolar electrodes as a first species of the second component 30, a second tip module with bipolar electrodes as a second species of the second component 50, and a third tip module with no electrosurgical electrodes as a third species of the second component 50, whereby the first to third tip modules can be interchangeably attached to the debrider handpiece to implement a debrider.

The surgical system 1-1 can further include a first drill bit (designed to be driven at a first speed) as a fourth species of the second component 50, and a second drill bit (designed to be driven at a second speed different from the first speed) as a fifth species of the second component 50, whereby the first drill bit and second drill bit can be interchangeably attached to the drill handpiece to implement a drill.

The first to fifth species of the second component 50 are each provided with a different species of the second target state identification circuit 1700. The different species of the second target state identification circuit 1700 can be implemented by, for example, capacitors with different ratings. Based on this distinction, the target state detection circuit 1310 is able to detect from the second attachment state signal the attachment of a tip/blade module to the first component 30 and also the specific species of tip/blade module attached to the first component 30.

The controller circuit 1370 is further configured to control the function module FM based on the detection of the attachment of the specific species of handpiece to the console 10 and the detection of the attachment of the specific species of tip/blade module to the specific species of handpiece.

In one example, the controller circuit 1370 is configured to control the function module FM to energize the detected first to third tips (including monopolar electrodes, bipolar electrodes, and no electrosurgical electrodes, respectively) differently based on the second attachment state signal.

In another example, the controller circuit 1370 is configured to control the function module FM to drive the detected first and second drill bits at the appropriate speed based on the second attachment state.

In yet another example, the controller circuit 1370 is configured to control the function module FM to prevent any action based on a second attachment state signal that indicates the species of tip/blade module and the species of handpiece attached to the console 10 are incompatible. That is, the controller circuit 1370 is configured to control the function module FM to prevent any action based on the second attachment state signal that indicates one of the first and second drill bits is attached to the debrider handpiece. Further, the controller circuit 1370 is configured to control the function module FM to prevent any action based on the second attachment state signal that indicates one of the first to third tip modules is attached to the drill handpiece.

SECOND EMBODIMENT

Figure 2:
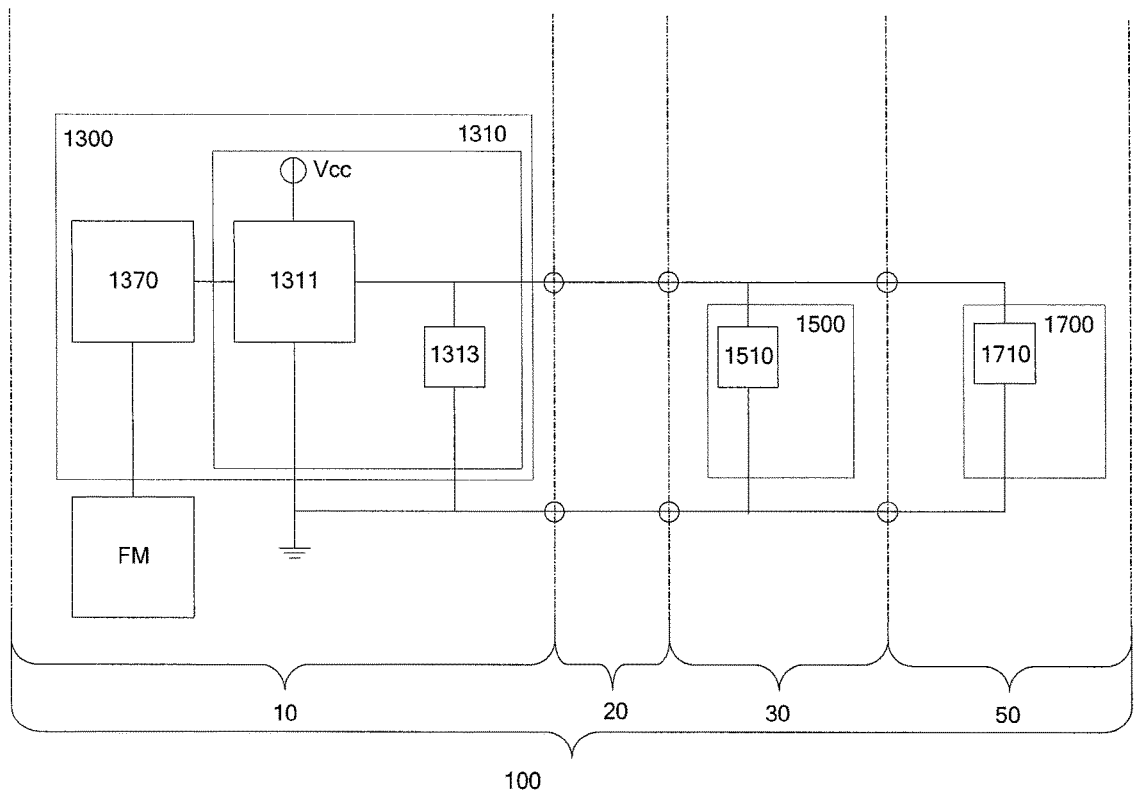
FIG. 2 shows a surgical system 1-2 according to a second embodiment of the present invention.

In a second embodiment, a surgical system 1-2 as shown in FIG. 2 is provided. The surgical system 1-2 is a modification of the surgical system 1-1 provided in the first embodiment.

The surgical system 1-2 further includes an intermediate component 20. In the surgical system 1-2, the intermediate component 20 is detachably attachable to the console 10, the first component 30 is detachably attachable to the intermediate component 20, and the second component 50 is detachably attachable to the first component 30.

The intermediate component 20, the first component 30, and the second component 50 can be implemented as a debrider. An example of the intermediate component 20 is a power cable that is detachably attachable to the console 10. An example of the first component 30 is the handpiece of the debrider that is detachably attachable to the power cable. An example of the second component 50 is the interchangeable tip/blade module of the debrider that is detachably attachable to the handpiece. The first embodiment differs from the second embodiment in that in the surgical system 1-1, a power cord and a handpiece are integrated and provided as a single first component 30 that is detachably attachable to the console 10.

In the target state control circuit 1300, the target state detection circuit 1310 is configured to detect at least: a baseline attachment state in which the first component 30 is not attached to the console 10 via the intermediate component 20; a first attachment state in which the first component 30 is attached to the console 10 via the intermediate component 20 and the second component 50 is not attached to the first component 30; and a second attachment state in which the first component 30 is attached to the console 10 via the intermediate component 20 and the second component 50 is attached to the first component 30.

In the baseline attachment state, the reference circuit 1313 is configured to output the baseline signal based on the detection signal, wherein the baseline signal indicates that the first component 30 is not attached to the console 10 via the intermediate component 20.

In the first attachment state, the reference circuit 1313 and the first target state identification circuit 1500 are electrically connected to the detection signal generation circuit 1311. Specifically, the first target state identification circuit 1500 is electrically connected to the detection signal generation circuit 1311 via the intermediate component 20 upon attachment of the intermediate component 20 to the console 10 and attachment of the first component 30 to the intermediate component 20. In an example, the console 10 and the intermediate component 20 are provided with one or more pin and socket connectors, and the intermediate component 20 and the first component 30 are provided with one or more pin and socket connectors to electrically connect the first target state identification circuit 1500 and the detection signal generation circuit 1311 upon attachment of the intermediate component 20 to the console 10 and attachment of the first component 30 to the intermediate component 20.

In the first attachment state, the reference circuit 1313 and the first target state identification circuit 1500 are configured to output the first attachment state signal based on the detection signal, wherein the first attachment state signal indicates that the first component 30 is attached to the console 10 via the intermediate component 20 and the second component 50 is not attached to the first component 30.

In the second attachment state, the reference circuit 1313, the first target state identification circuit 1500, and the second target state identification circuit 1700 are electrically connected to the detection signal generation circuit 1311 upon attachment of the intermediate component 20 to the console 10, attachment of the first component 30 to the intermediate component 20, and attachment of the second component 50 to the first component 30. In an example, the first component 30 and the second component 50 are provided with one or more pin and socket connectors to electrically connect the second target state identification circuit 1700 to the detection signal generation circuit 1311 upon attachment of the second component 50 to the first component 30.

In the second attachment state, the reference circuit 1313, the first target state identification circuit 1500 and the second target state identification circuit 1700 are configured to output the second attachment state signal based on the detection signal, wherein the second attachment state signal indicates that the first component 30 is attached to the console 10 via the intermediate component 20 and the second component 50 is attached to the first component 30.

As in the first embodiment, the controller circuit 1370 in the second embodiment is configured to control the function module FM based on the target state detected by the target state detection circuit 1310. Specifically, the controller circuit 1370 is configured to control the function module FM based on one or more of the baseline signal, the first attachment state signal, and the second attachment state signal.

In the second embodiment, the surgical system 1-2 is not limited to a single intermediate component. The surgical system 1-2 can include n intermediate components (where n is an integer equal to or greater than 2). In one example, a first intermediate component (e.g., an adaptor) is detachably attachable to the console 10, a second intermediate component (e.g., a power cord) is detachably attachable to the first intermediate component, and the first component 30 is detachably attachable to the second intermediate component. In another example, a first intermediate component is detachably attachable to the console 10, a second intermediate component is detachably attachable to the console 10, and the first component 30 is detachably attachable to both the first intermediate component and the second intermediate component.

In a modification of the second embodiment, the surgical system 1-2 can also include an intermediate component 20 adapted to be detachably attachable to the first component 30 and the second component 50. An example of the intermediate component 20 in the modification is gear reducing gear box that is detachably attachable to the first component 30 and the second component 50. Specifically, the speed reducing gear box is detachably attachable to a drive shaft in the handpiece comprising the first component 30 and detachably attachable to a rotating bit comprising the second component 50. In the modification, the surgical system 1-2 is not limited to a single intermediate component. The surgical system 1-2 can include a plurality of intermediate components connecting the first component 30 and the second component 50. As an example, the above-described gear reducing gear box can be implemented as two or more separate assemblies corresponding to two or more intermediate components. In the second attachment state, the reference circuit 1313, the first target state identification circuit 1500, and the second target state identification circuit 1700 are electrically connected to the detection signal generation circuit 1311 upon attachment of the first component 30 to the console 10, attachment of the intermediate component 20 to the first component 30, and attachment of the second component 50 to the intermediate component 20. In the second attachment state, the reference circuit 1313, the first target state identification circuit 1500, and the second target state identification circuit 1700 are configured to output the second attachment state signal based on the detection signal, wherein the second attachment state signal indicates that the first component 30 is attached to the console 10, and the second component 50 is attached to the first component 30 via the intermediate component 20.

In a further modification of the second embodiment, the surgical system 1-2 can include one or more intermediate components between the console 10 and the first component 30, and one or more intermediate components between the first component 30 and the second component 50.

In the above-provided description of the second embodiment and modifications thereof, the one or more intermediate components are different from the first component 30 and the second component 50 in that the one or more intermediate components are not provided with an identification circuit such as the identification circuit 1500 provided to the first component 30 and the identification circuit 1700 provided to the second component 50. Accordingly, the surgical system 1-2 can include x components (including the first component 30, the second component 50, and one or more intermediate components), and the surgical system 1-2 can detect the baseline attachment state and y attachment states (here, a first attachment state and the second attachment state) where x is greater than y.

THIRD EMBODIMENT

In a third embodiment, a surgical system 1-3 as shown in FIG. 3 is provided. The surgical system 1-3 is based on the surgical system 1-1 of the first embodiment. FIG. 3 shows an example of the circuit 100 implemented with an astable oscillator circuit (or more generally, a capacitive sensing circuit).

In the third embodiment, the astable oscillator circuit is implemented with a 555 timer integrated circuit (IC). The frequency and waveform of an astable oscillator output signal on a line 103 is controlled by the fixed electrical connection to the reference circuit 1313 including a reference capacitor 1315, and one or more of: (i) the electrical connection of the first target state identification circuit 1500 (including a first attachment state capacitor 1510) upon attachment of the first component 30 to the console 10, and (ii) the electrical connection of the second target state identification circuit 1700 (including a second attachment state capacitor 1710) upon attachment of the second component 50 to the first component 30. The astable oscillator's output signal frequency is determined by the capacitance offered by the reference capacitor 1313, the first attachment state capacitor 1510, and the second attachment state capacitor 1710. More specifically, the astable oscillator's output signal frequency is indirectly proportional to the capacitance offered by the reference capacitor 1313, the first attachment state capacitor 1510, and the second attachment state capacitor 1710.

As shown in FIG. 3, the trigger pin 2 and the threshold pin 6 are connected so as to form a self-trigger, causing the 555 timer IC to operate as an astable oscillator. Here, resistor R1 and resistor R2 act as timing resistors and the discharge pin 7 is connected to the junction of resistor R1 and resistor R2.

When the supply Vcc is connected, the reference capacitor 1315, and the selectively electrically connected first attachment state capacitor 1510, and the selectively electrically connected second attachment state capacitor 1710 act like a timing capacitor and charge toward Vcc. When the one or more capacitors get charged, the output pin 3 is held high. When the one or more capacitors voltage is just greater than ($\frac{2}{3}$) Vcc, the upper comparator of the 555 timer IC triggers the internal control flip flop and the one or more capacitors discharge towards the ground through resistor R2. During this discharge cycle the output is held low. During this discharge, as the voltage across the one or more capacitors reaches ($\frac{1}{3}$) Vcc the lower comparator is triggered and again it starts charging and the output is held high.

As additional capacitors are electrically connected in parallel, the offered capacitance increases, thereby changing the frequency of the astable oscillator output. More specifically, as additional capacitors are electrically connected in parallel, the offered capacitance increases, thereby decreasing the frequency of the astable oscillator output. Based on the predetermined ratings of the reference capacitor 1313, the first attachment state capacitor 1510, and the second attachment state capacitor 1710, the frequency of the astable oscillator output can be utilized to determine the baseline attachment state, the first attachment state and the second attachment state. As discussed above with respect to the first embodiment, based on the predetermined ratings of the first attachment state capacitor 1510 and the second attachment state capacitor 1710, the frequency of the astable oscillator output can be utilized to determine not only the attachment of one or more of the first component 30 and the second component 50 but also the species of the attached first component 30 and the species of the attached second component 50

The output signal of the astable oscillator from pin 3 is referred to herein as a feedback signal. The feedback signal can be a square wave. In the baseline attachment state where the first component 30 is not attached to the console 10, the reference capacitor 1315 is selected such that the astable oscillator provides a feedback signal having a measurable baseline frequency (as the baseline signal). In the first attachment state where the first component 30 is attached to the console 10, the first attachment state capacitor 1510 is selected such that the astable oscillator provides a feedback signal having a measurable first frequency (as the first attachment state signal) that is different from the baseline frequency. In the second attachment state where the first component 30 is attached to the console 10 and the second component 50 is attached to the first component 30, the second target state capacitor 1710 is selected such that the astable oscillator provides a feedback signal having a measurable second frequency (as the second attachment state signal) that is different from the baseline frequency and the first attachment state frequency. The controller circuit 1370 is then configured to determine the capacitance provided in the astable oscillator by, for example, counting the pulses of the square wave in a predetermined time period. The determined capacitance then indicates the baseline attachment state, the first attachment state, and the second attachment state in the surgical system 1-3.

It is noted that even in the absence of an attachment of the first component 30 to the console 10, the surgical system 1-3 and in particular the circuit 100 provides for the reference circuit 1313 including the reference capacitor 1315 in the console 10 such that the baseline signal (feedback signal) based on the baseline frequency is provided to the controller circuit 1370. Thereby, the controller circuit 1370 is able to control the function module FM based on the baseline attachment state.

FOURTH EMBODIMENT

In a fourth embodiment, a surgical system 1-4 as shown in FIG. 4 is provided. The surgical system 1-4 is based on the surgical system 1-1 of the first embodiment and the surgical system 1-3 of the third embodiment. FIG. 4 shows another example of the circuit 100 implemented with an astable oscillator circuit.

In the fourth embodiment, the astable oscillator circuit can be implemented by replacing the reference capacitor 1315 with a reference resistor, and replacing the one or more of the first attachment state capacitor 1510 and the second attachment state capacitor 1710 with a corresponding one or more of a first attachment state resistor 1510 and a second attachment state resistor 1710.

As shown in FIG. 4, the detection signal generation circuit 1311 includes a resistor 501, a resistor 502, a comparator 503, an inverting Schmidt trigger 504 for hysteresis, a reset transistor 506, and a capacitor 510.

In the detection signal generation circuit 1311, a reference voltage from a voltage divider including the resistor 501 and 502 connected between a supply voltage Vcc and ground on bus 105 is provided.

FIG. 4 shows an astable oscillator as a relaxation oscillator. A comparator takes in and compares a reference voltage from a voltage divider and the device state signal, and sends the output to a resetting latch which provides feedback to the comparator to provide the feedback signal to the controller. The resetting latch is comprised of a Schmidt trigger to provide hysteresis and a transistor switch to reset the oscillation.

In FIG. 4, a reference resistor 1315, a first attachment state resistor 1510, and a second attachment state resistor 1710 replace the reference capacitor 1315, the first attachment state capacitor 1510, and the second attachment state capacitor 1710, respectively, described above with respect to FIG. 3.

FIFTH EMBODIMENT

In a fifth embodiment, a surgical system 1-5 as shown in FIG. 5 is provided. The surgical system 1-5 is based on the surgical system 1-1 of the first embodiment. FIG. 5 shows an example of the circuit 100 implemented with a voltage sensor.

In the target state detection circuit 1310, the detection signal generation circuit 1311 and the reference resistor 1315 are provided. The detection signal generation circuit 1311 includes an analog-to-digital converter (ADC) 521, a comparator 522, and resistors 501, 502, 511 and 520. The first target state identification circuit 1500 includes a first attachment state resistor 1510. The second target state identification circuit 1700 includes a second attachment state resistor 1710.

A voltage divider including the resistor 511, the reference resistor 1315, the selectively electrically connected first attachment state resistor 1510, and the selectively electrically connected second attachment state resistor 1710 with the supply voltage Vcc applied across the resistors is provided. A target state voltage from the connection between the resistor 511 and the reference resistor 1315 (and the first attachment state resistor 1510 and the second attachment state resistor 1710) is provided on line 106 to the comparator 522.

A voltage divider including the resistor 501 and the resistor 502 with the supply voltage Vcc applied across the resistors is provided. A reference voltage from the connection between the resistor 501 and the resistor 502 is provided to the comparator 522.

The target state voltage and the reference voltage are compared by comparator 522. Stability of the comparison is provided by the resistor 520. The ADC 521 receives an output of the comparator 522 and provides a feedback signal indicating one of a baseline attachment state, a first attachment state, and a second attachment state on line 103 to the controller circuit 1370. Thereby, the controller circuit 1370 controls the function module FM based on the feedback signal.

SIXTH EMBODIMENT

Figure 6:
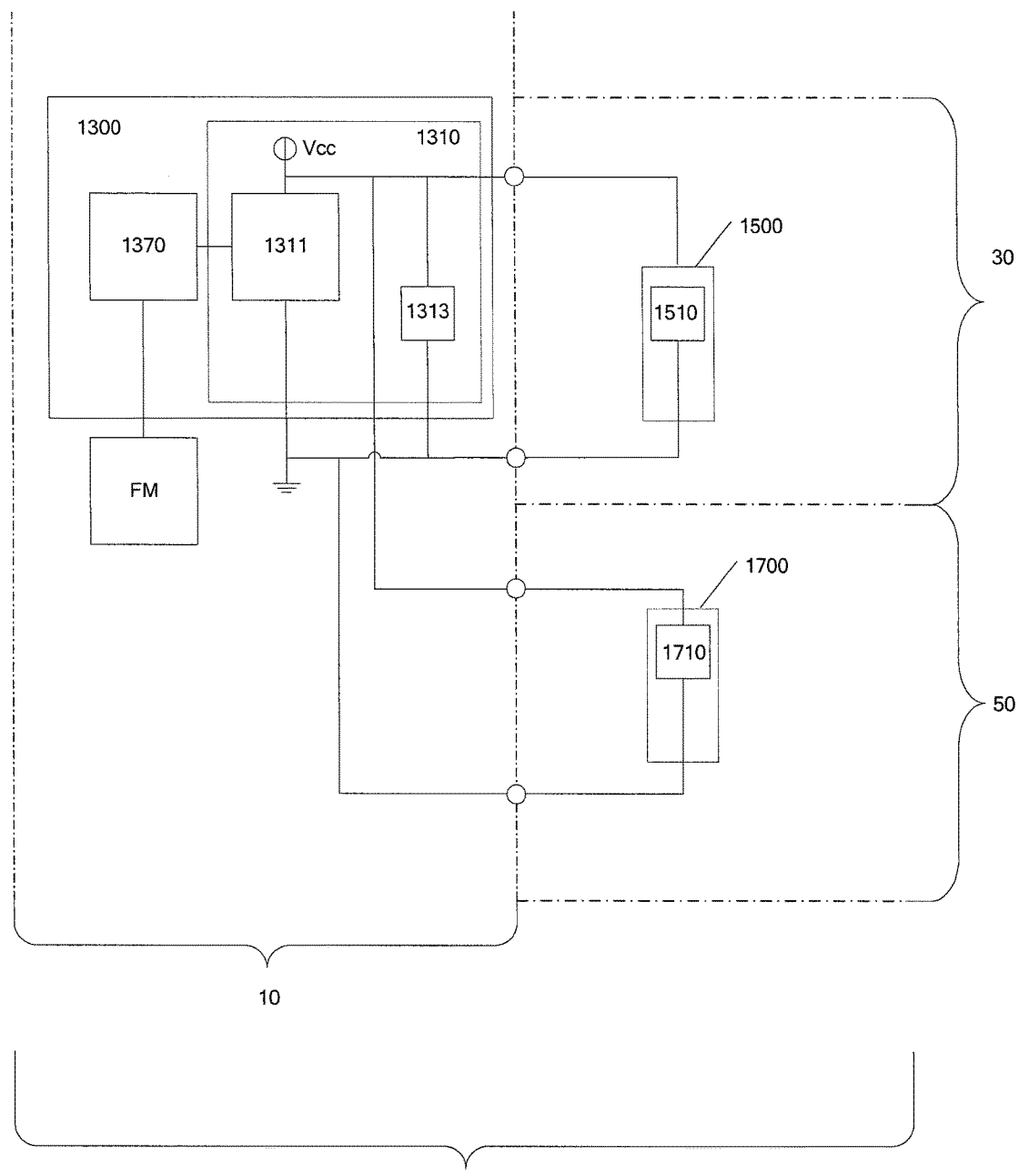
FIG. 6 shows a surgical system 1-6 according to a sixth embodiment of the present invention.

In a sixth embodiment, a surgical system 1-6 as shown in FIG. 6 is provided. The surgical system 1-6 includes a console 10, a first component 30 that is detachably attachable to the console 10, and a second component 50 that is also detachably attachable to the console 10.

The first component 30 and the second component 50 can be implemented as independent modules that are detachably attachable to the console 10. An example of the first component 30 is a handpiece of a debrider. An example of the second component 50 is an input unit such as a foot pedal for receiving one or more inputs from a user.

The surgical system 1-6 further includes a circuit 100 that is distributively arranged to the console 10, the first component 30 and the second component 50. The circuit 100 includes a function module FM, a target state control circuit 1300, a first target state identification circuit 1500, and a second target state identification circuit 1700.

The function module FM and the target state control circuit 1300 are arranged in the console 10. The first target state identification circuit 1500 is arranged in the first component 30. The second target state identification circuit 1700 is arranged in the second component 50.

The target state control circuit 1300 includes a target state detection circuit 1310 configured to detect at least one of the following target states: a baseline attachment state in which the first component 30 is not attached to the console 10 and the second component 50 is not attached to the console 10; a first attachment state in which the first component 30 is attached to the console 10 and the second component 50 is not attached to the console 10; a second attachment state in which the first component 30 is attached to the console 10 and the second component 50 is attached to the console 10; and a third attachment state in which the first component 30 is not attached to the console 10 and the second component 50 is attached to the console 10.

The target state control circuit 1300 further includes a controller circuit 1370 that can be implemented by hardware or a combination of hardware and software. The controller circuit 1370 is configured to control the function module FM based on the target state detected by the target state detection circuit 1310. Specifically, the controller circuit 1370 is configured to control the function module FM based on the one or more of the first to third attachment states detected by the target state detection circuit 1310.

The target state detection circuit 1310 includes a detection signal generation circuit 1311 configured to provide a detection signal. The target state detection circuit 1310 further includes a reference circuit 1313 that is arranged to the console 10. The reference circuit 1313 is further arranged to be electrically connected to the detection signal generation circuit 1311.

In the baseline attachment state, the reference circuit 1313 is configured to provide a baseline signal based on the detection signal, wherein the baseline signal indicates that the first component 30 is not attached to the console 10 and that the second component 50 is also not attached to the console 10.

In the first attachment state, the reference circuit 1313 and the first target state identification circuit 1500 are electrically connected to the detection signal generation circuit 1311. Specifically, the first target state identification circuit 1500 is electrically connected to the detection signal generation circuit 1311 upon attachment of the first component 30 to the console 10. In an example, the console 10 and the first component 30 are provided with one or more pin and socket connectors to electrically connect the first target state identification circuit 1500 and the detection signal generation circuit 1311 upon attachment of the first component 30 to the console 10.

In the first attachment state, the reference circuit 1313 and the first target state identification circuit 1500 are configured to provide a first attachment state signal based on the detection signal, wherein the first attachment state signal indicates that the first component 30 is attached to the console 10 and the second component 50 is not attached to the console 10.

In the second attachment state, the reference circuit 1313, the first target state identification circuit 1500, and the second target state identification circuit 1700 are electrically connected to the detection signal generation circuit 1311 upon attachment of the first component 30 to the console 10 and attachment of the second component 50 to the console 10. In an example, the console 10 and the second component 50 are provided with one or more pin and socket connectors to electrically connect the second target state identification circuit 1700 to the detection signal generation circuit 1311 upon attachment of the second component 50 to the console 10.

In the second attachment state, the reference circuit 1313, the first target state identification circuit 1500 and the second target state identification circuit 1700 are configured to provide a second attachment state signal based on the detection signal, wherein the second attachment state signal indicates that the first component 30 is attached to the console 10 and the second component 50 is also attached to the console 10.

In the third attachment state, the reference circuit 1313 and the second target state identification circuit 1700 are electrically connected to the detection signal generation circuit 1311 upon attachment of the second component 50 to the console 10.

In the third attachment state, the reference circuit 1313 and the second target state identification circuit 1700 are configured to provide a third attachment state signal based on the detection signal, wherein the third attachment state signal indicates that the second component 30 is attached to the console 10 and the first component 30 is not attached to the console 10.

The controller circuit 1370 is configured to control the function module FM based on the output of one of the baseline signal, the first attachment state signal, the second attachment state signal, and the third attachment state signal.

In a modification of the sixth embodiment, one or more intermediate components (similar to the ones described in the second embodiment) can be provided between the first component 30 and the console 10, and one or more intermediate components (similar to the ones described in the second embodiment) can be provided between the second embodiment 50 and the console 10.

SEVENTH EMBODIMENT

Figure 7:
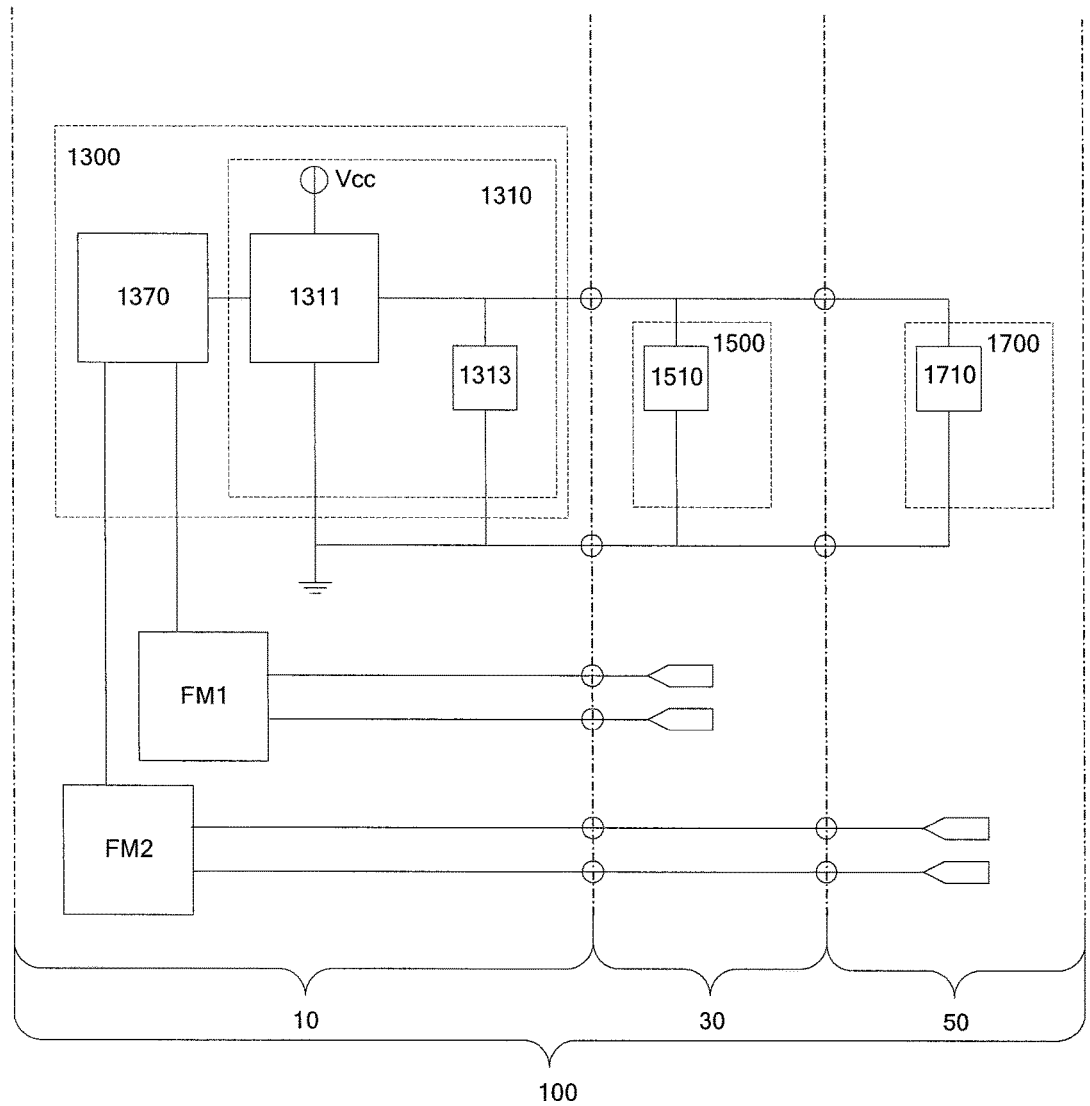
FIG. 7 shows a surgical system 1-7 according to a seventh embodiment of the present invention.

In a seventh embodiment, a surgical system 1-7 as shown in FIG. 7 is provided. The surgical system 1-7 is a modification of the surgical system 1-1 provided in the first embodiment.

The surgical system 1-7 includes a first function module FM1 and a second function module FM2 arranged in the console 10 instead of the function module FM described in the first embodiment.

The first function module FM1 can include a first therapy signal generator configured to generate a first therapy signal that is passed to the first component 30 for performing a first therapeutic function.

The second function module FM2 can include a second therapy signal generator configured to generate a second therapy signal that is passed to the second component 50 via the first component 30 for performing a second therapeutic function.

In the surgical system 1-7, the controller circuit 1370 is configured to control the first function module FM1 and the second function module FM2 based on one or more of the baseline signal, the first attachment state signal, and the second attachment state signal. The controller circuit 1370 is configured to control the first therapy signal generator of the first function module FM1 to generate the first therapy signal based on one or more of the baseline signal, the first attachment state signal, and the second attachment state signal. Further, the controller circuit 1370 is configured to control the second therapy signal generator of the second function module FM2 to generate the second therapy signal based on one or more of the baseline signal, the first attachment state signal, and the second attachment state signal.

In a modification of the seventh embodiment, the first component 30 can be a handpiece of a debrider, and the first function module FM1 can include a signal generator to control a device such as an irrigation valve and/or a suction valve arranged in the handpiece. The controller circuit 1370 is configured to control the signal generator of the first function module FM1 based on one or more of the baseline signal, the first attachment state signal, and the second attachment state signal, to open, close, and other control of the irrigation valve and/or suction valve arranged in the handpiece.

EIGHTH EMBODIMENT

Figure 8:
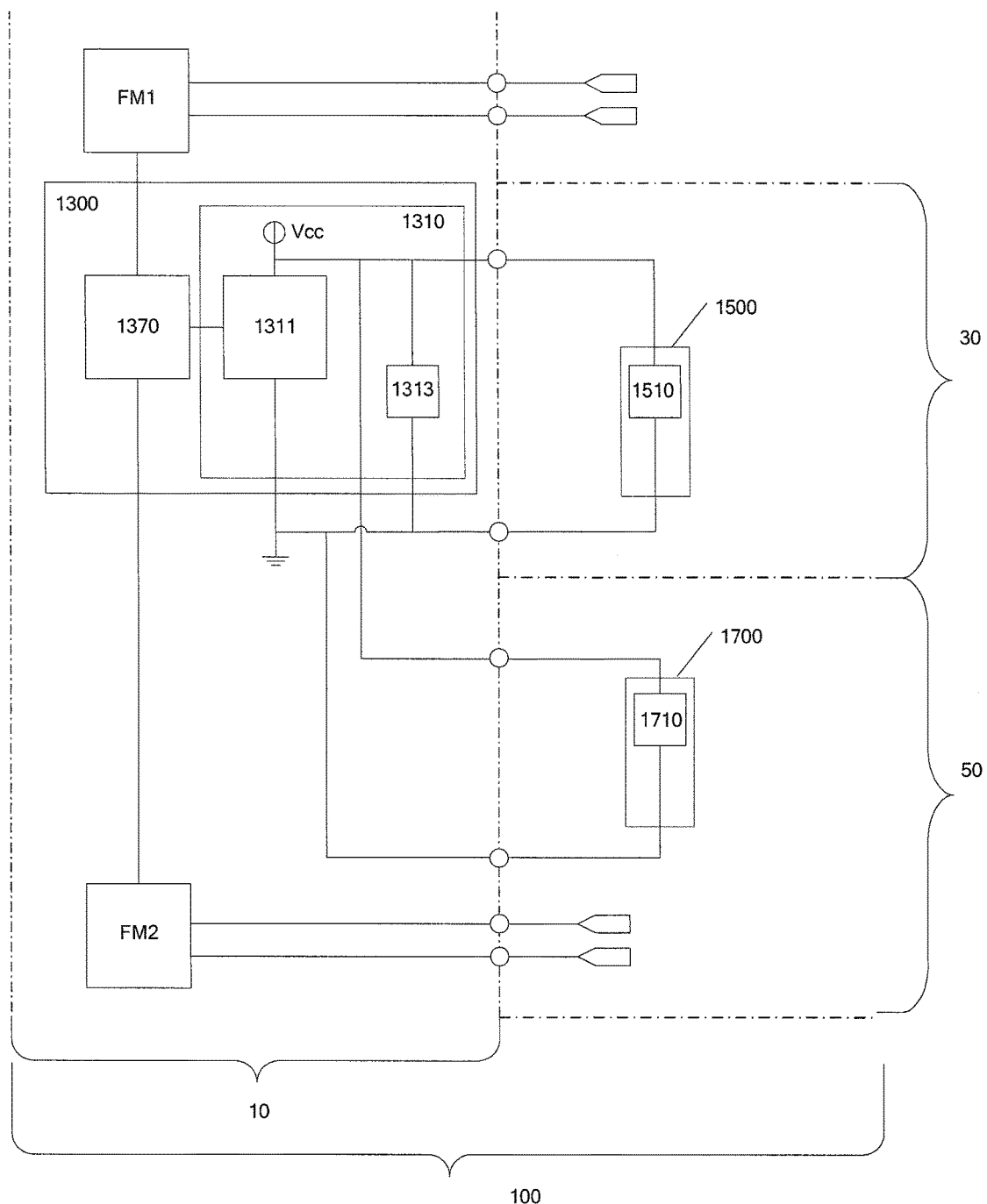
FIG. 8 shows a surgical system 1-8 according to an eighth embodiment of the present invention.

In an eighth embodiment, a surgical system 1-8 as shown in FIG. 8 is provided. The surgical system 1-8 is a modification of the surgical system 1-6 provided in the sixth embodiment.

The surgical system includes a first function module FM1 and a second function module FM2 arranged in the console 10 instead of the function module FM described in the sixth embodiment.

The first function module FM1 can include a first therapy signal generator configured to generate a first therapy signal that is passed to the first component 30 for performing a first therapeutic function.

The second function module FM2 can include a second therapy signal generator configured to generate a second therapy signal that is passed to the second component 50 for performing a second therapeutic function.

In the surgical system 1-8, the controller circuit 1370 is configured to control the first function module FM1 and the second function module FM2 based on one or more of the baseline signal, the first attachment state signal, the second attachment state signal, and the third attachment state signal. The controller circuit 1370 is configured to control the first therapy signal generator of the first function module FM1 to generate the first therapy signal based on one or more of the baseline signal, the first attachment state signal, and the second attachment state signal. Further, the controller circuit 1370 is configured to control the second therapy signal generator of the second function module FM2 to generate the second therapy signal based on one or more of the baseline signal, the first attachment state signal, and the second attachment state signal.

NINTH EMBODIMENT

Figure 9:
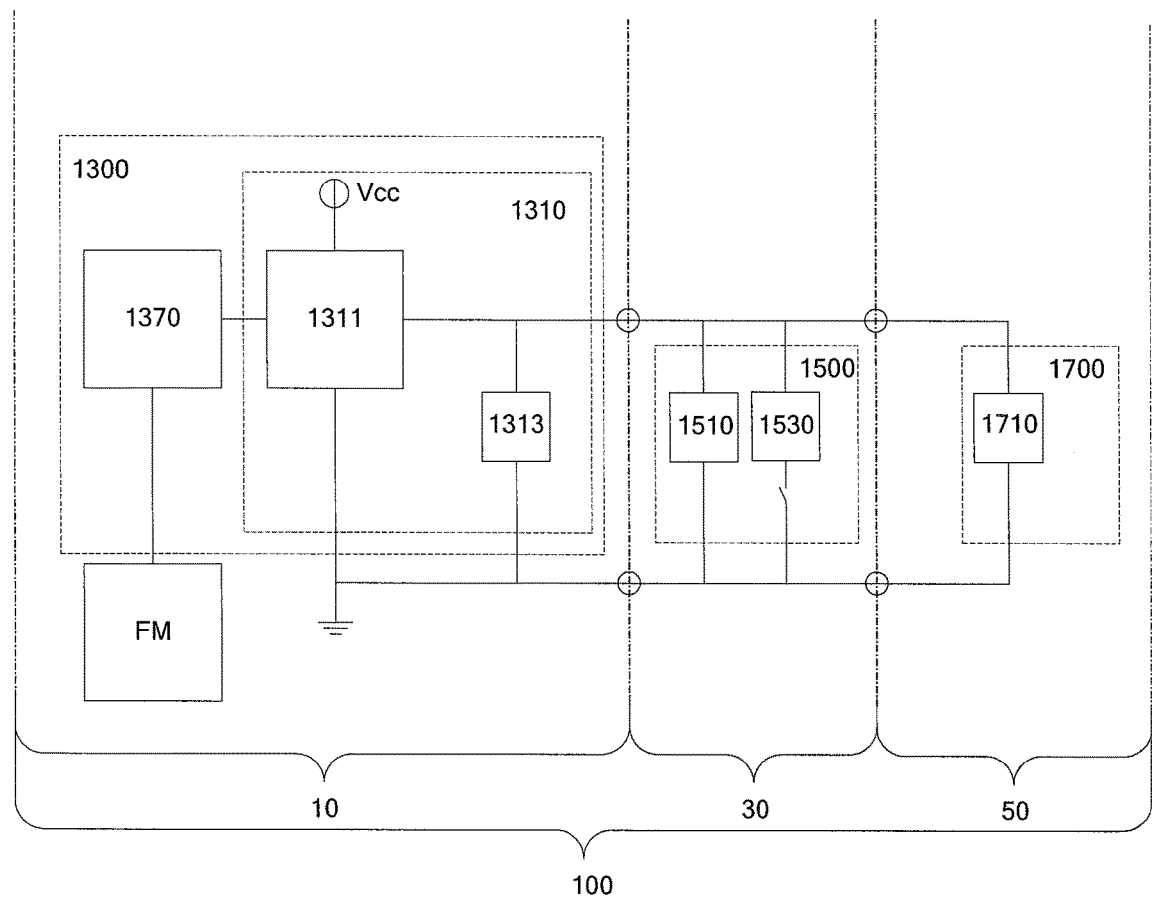
FIG. 9 shows a surgical system 1-9 according to a ninth embodiment of the present invention.

In a ninth embodiment, a surgical system 1-9 as shown in FIG. 9 is provided. The surgical system 1-9 is based on the surgical system 1-1 of the first embodiment and the surgical system 1-3 of the third embodiment.

In the surgical system 1-9, the first target state identification circuit 1500 includes a first attachment state circuit 1510 and further includes a first switch identification circuit 1530 and a first switch 1550. The first switch identification circuit 1530 is electrically connected to the detection signal generation circuit 1311 upon attachment of the first component 30 to the console 10 and actuation of the first switch 1550 by the user.

In the first attachment state where the first switch 1550 is not actuated by the user, the reference circuit 1313 and the first attachment state circuit 1510 are configured to provide the first attachment state signal based on the detection signal, wherein the first attachment state signal indicates that the first component 30 is attached to the console 10, the second component 50 is not attached to the first component 30, and the first switch 1550 is not actuated by the user.

In the first attachment state where the first switch 1550 is actuated by the user, the reference circuit 1313, the first attachment state circuit 1510, and the first switch identification circuit 1530 are configured to provide a first switch signal based on the detection signal, wherein the first switch signal indicates that the first component 30 is attached to the console 10, the second component 50 is not attached to the first component 30, and the first switch 1550 is actuated by the user.

In the surgical system 1-9, the controller circuit 1370 is further configured to control the function module FM based on the first switch signal.

TENTH EMBODIMENT

Figure 10:
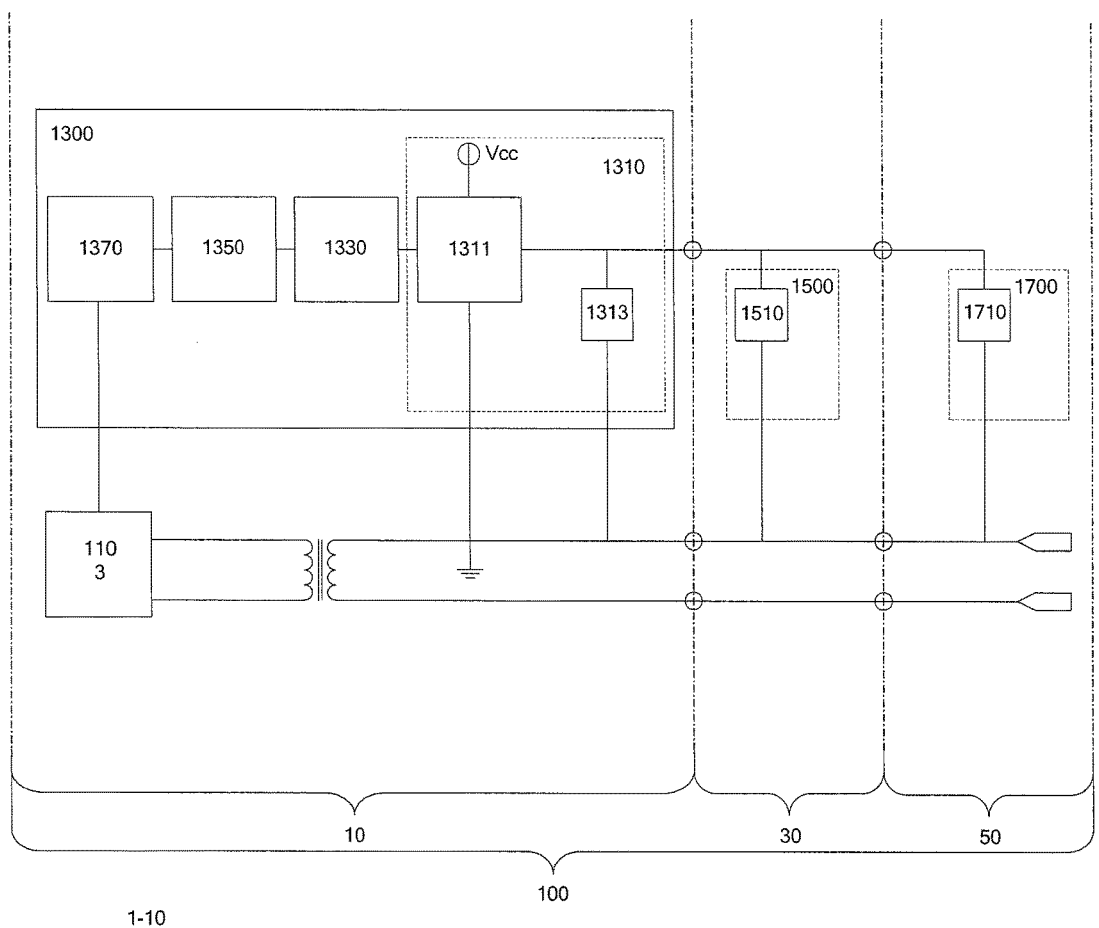
FIG. 10 shows a surgical system 1-10 according to a tenth embodiment of the present invention.

In a tenth embodiment, a surgical system 1-10 as shown in FIG. 10 is provided. The surgical system 1-10 is based on the surgical system 1-1 of the first embodiment, the surgical system 1-3 of the third embodiment, and the surgical system 1-4 of the fourth embodiment.

The surgical system 1-10 further includes an alternating current (AC) signal generator 1103 and a step-up transformer 1105 that are arranged in the console 10, and a pair of electrical leads 1107, 1109 that are distributively arranged across the console 10, the first component 30, and the second component 50.

The AC signal generator 1103 provides a time varying signal and more specifically, an AC signal to a low voltage side of the step-up transformer 1105. The step-up transformer 1105 steps up a voltage of the AC signal to a high voltage, and outputs the high voltage AC signal on a high voltage side of the step-up transformer 1105 to the pair of electrical leads 1107, 1109. The high voltage AC signal is characterized by a least one of a frequency and a voltage that is desirable for one or more therapeutic functions performed by the second component 50. The high voltage AC signal is referred to herein as a "therapy signal." The therapy signal may range, for example, from about 150 V to about 1500 V, with frequencies ranging from about 10 kHz to about 500 kHz.

In the circuit 100, the detection signal generation circuit 1311 provides the detection signal that is referenced to one of the electrical leads 1107 and 1109. Based on this implementation, the circuit 100 is capable of detecting the selective electrical connection of the first target state identification circuit 1500 and the second target state identification circuit 1700, and passing the therapy signal to the second component 50 with an arrangement of three pins and connectors provided to the console 10 and the first component 30, and three pins and connectors provided to the first component 30 and the second component 50 in the limited structural interface between console 10 and the first component 30 and the limited structural interface between the first component 30 and the second component 50.

The target state control circuit 1300 further includes an analog-to-digital converter (ADC) 1330 and an electrical isolation circuit 1350. The ADC 1330 is configured to convert the baseline state signal, the first attachment state signal, and the second attachment state signal to a digital signal. The digital signal is then passed through the electrical isolation circuit 1350 as a low voltage signal to the controller circuit 1370. Examples of the electrical isolation circuit 1350 include an opto-isolator, a capacitive isolator, and an inductive isolator.

The controller circuit 1370 is then configured to determine the capacitance provided in the astable oscillator based on the low voltage signal. The determined capacitance then indicates the detected target state. Further the controller circuit 1370 is configured to control the AC signal generator 1103 based on the determined detected target state.

ELEVENTH EMBODIMENT

Figure 11:
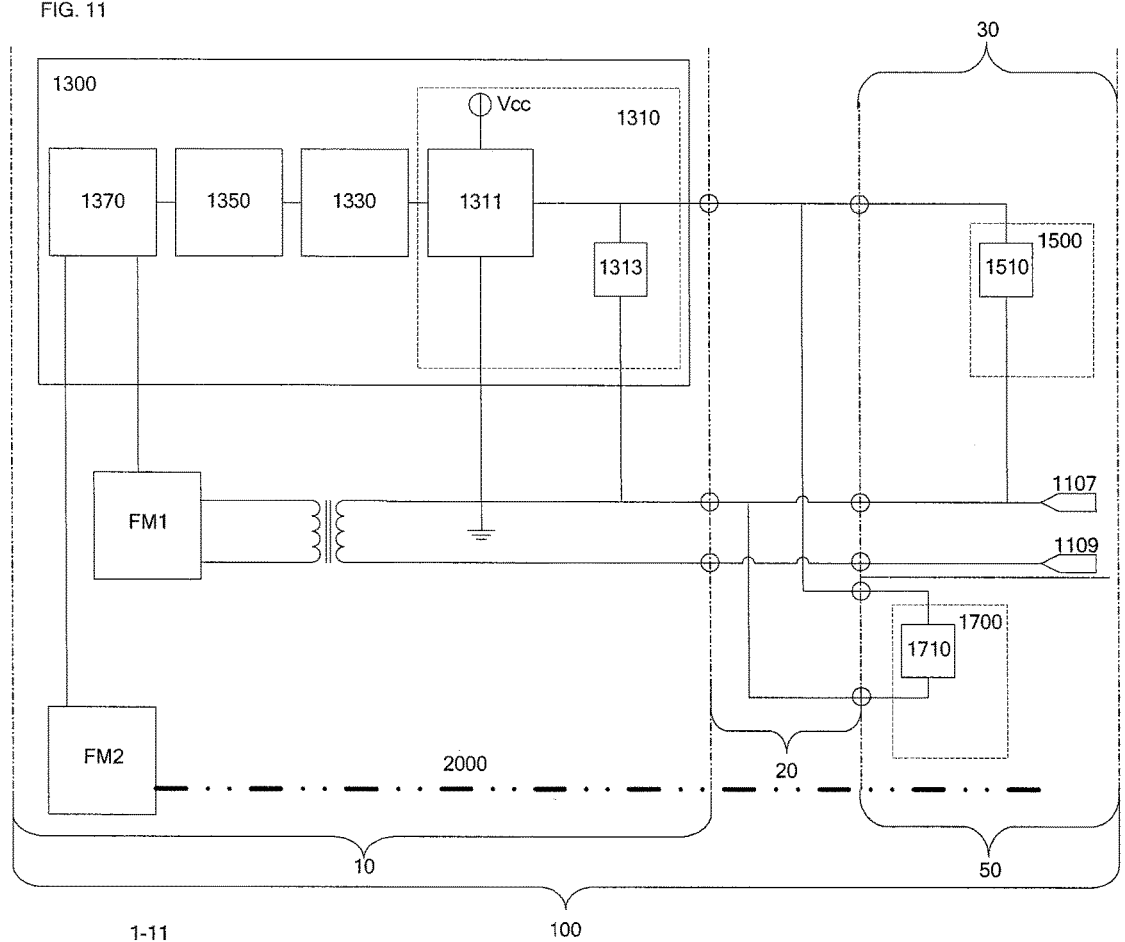
FIG. 11 shows a surgical system 1-11 according to an eleventh embodiment of the present invention.

In an eleventh embodiment, a surgical system 1-11 as shown in FIG. 11 is provided. The surgical system 1-11 is based on the surgical system 1-1 of the first embodiment, the surgical system 1-2 of the second embodiment, the surgical system 1-6 of the sixth embodiment, the surgical system 1-8 of the eighth embodiment, and the surgical system 1-10 of the tenth embodiment.

In the surgical system 1-11, the console 10 includes the target state control circuit 1300, the AC signal generator 1103 (as a first function module FM1), and the step-up transformer 1105, as described in the tenth embodiment. The console 10 further includes a second function module FM2.

The surgical system 1-11 includes an intermediate component 20 similar to that described in the second embodiment. The intermediate component 20 is provided to be detachably attachable to the console 10. The surgical system 1-11 further includes a first component 30 and a second component 50, similar to that described in the sixth embodiment and the eighth embodiment. The first component 30 is detachably attachable to the intermediate component 20. The second component 50 is also detachably attachable to the intermediate component 20.

The surgical system 1-11 further includes a fluid tube 2000 arranged to the second component 50. The fluid tube 2000 includes a distal end opening and a proximal end opening in fluid communication with the distal end. The fluid tube 2000 is further connected to the second function module FM2. The second function module FM2 can include one or more pumps and one or more valves that can be controlled by the controller circuit 1370. In one example, the second function module FM2 can be controlled to pump a fluid from a fluid source in the console 10 through the proximal end opening of the fluid tube 2000 and out from the distal end opening of the fluid tube 2000 to irrigate a tissue. In another example, the second function module FM2 can be controlled to provide suction to remove a fluid from the distal end opening of the fluid tube 2000 through the proximal end opening of the fluid tube 2000 and out to a fluid receptacle of the console 10. The surgical system 1-11 can further include additional fluid tubes similar to the fluid tube 2000, and the second function module FM2 can similarly be controlled by the controller circuit 1370 to pump or suction a fluid through the additional fluid tubes.

The distal end opening of the fluid tube 2000 can be further arranged to be in fluid communication with additional tubing in one or more of the intermediate component 20 and the first component 30. In an example, the intermediate component 20 can be a handpiece of a debrider and the first component 30 can be an interchangeable tip/blade module of the debrider.

The interchangeable tip/blade module can include a tip/blade module tubing having a proximal end that is detachably attachable to the distal end opening of the fluid tube 2000 and a distal opening that is in fluid communication with the proximal end opening of the tip/blade module tubing. The distal end opening of the tip/blade module tubing is arranged to be in fluid communication with the proximal end opening of the fluid tube 2000 upon attachment of the second component 50 to the handpiece of the intermediate component 20 and attachment of the handpiece of the intermediate component 20 to the tip/blade module of the first component 30.

As described in previous embodiments, in the baseline attachment state, the reference circuit 1313 is configured to output a baseline signal based on the detection signal. In surgical system 1-11, the baseline signal indicates that the first component 30 is not attached to the console 10 via the intermediate component 20 and that the second component 50 is not attached to console 10 via the intermediate component 20.

Similar to previously described embodiments, in the first attachment state, the reference circuit 1313 and the first target state identification circuit 1500 are electrically connected to the detection signal generation circuit 1311. Specifically, the first target state identification circuit 1500 is electrically connected to the detection signal generation circuit 1311 upon attachment of the intermediate component 20 to the console 10 and attachment of the first component 30 to the intermediate component 20.

In the first attachment state, the reference circuit 1313 and the first target state identification circuit 1500 are configured to output a first attachment state signal based on the detection signal, wherein the first attachment state signal indicates that the first component 30 is attached to the console 10 via the intermediate component 20 and the second component 50 is not attached to the console 10 via the intermediate component 20.

Similar to previously described embodiments, in the second attachment state, the reference circuit 1313, the first target state identification circuit 1500, and the second target state identification circuit 1700 are electrically connected to the detection signal generation circuit 1311 upon attachment of the intermediate component 20 to the console 10, attachment of the first component 30 to the intermediate component 20, and attachment of the second component 50 to the intermediate component 20.

In the second attachment state, the reference circuit 1313, the first target state identification circuit 1500, and the second target state identification circuit 1700 are configured to output a second attachment state signal based on the detection signal, wherein the second attachment state signal indicates that the first component 30 is attached to the console 10 via the intermediate component 20 and the second component 50 is attached to the console 10 via the intermediate component 20.

Similar to previously described embodiments, in the third attachment state, the reference circuit 1313 and the second target state identification circuit 1700 are electrically connected to the detection signal generation circuit 1311 upon attachment of the intermediate component 20 to the console 10 and attachment of the second component 50 to the intermediate component 20.

In the third attachment state, the reference circuit 1313 and the second target state identification circuit 1700 are configured to provide a third attachment state signal based on the detection signal, wherein the third attachment state signal indicates that the second component 50 is attached to the console 10 via the intermediate component 20 and the first component 30 is not attached to the console 10 via the intermediate component 20.

The controller circuit 1370 is configured to control the first function module FM1 to generate the therapy signal passed to the electrical leads 1107, 1109 based on one or more of the baseline signal, the first attachment state signal, the second attachment state signal, and the third attachment state signal. Further, the controller circuit 1370 is configured to control the second function module FM2 to provide irrigation, suction, or both through the fluid tube 2000 based on one or more of the baseline signal, the first attachment state signal, the second attachment state signal, and the third attachment state signal.

In an example, upon receiving an instruction inputted by a user to control the first function module FM1 to generate the therapy signal, and/or to control the second function module FM2 to provide irrigation, suction, or both, the controller circuit 1370 initially determines which of the baseline signal, the first attachment state signal, the second attachment state signal, and the third attachment state signal is provided.

The controller circuit 1370 is configured to control the first function module FM1 to generate the therapy signal and to control the second function module FM2 to provide irrigation, suction, or both only after determining that the second attachment state signal is provided. That is, therapy signal is generated and fluid irrigation, suction, or both are provided only after confirmation that the interchangeable tip/blade module of the first component 30 is attached to the console 10 via the handpiece of the intermediate component 20 and confirmation that the second component 50 (including the fluid tube 2000) is attached to the handpiece of the intermediate component 20. The described control performed by the controller circuit 1370 is thus capable of preventing the generation of the therapy signal by the first function module FM1 and the activation of irrigation, suction, or both by the second function module FM2 upon an inadvertent instruction by a user to generate the therapy signal and provide irrigation, suction, or both based on a determination that one of a baseline signal (indicating that neither the first component 30 nor the second component 50 is attached), a first attachment state signal (indicating that the first component 30 is attached to the console 10 via the intermediate component 20 and the second component 50 is not attached to the console 10 via the intermediate component 20), and the third attachment state signal (indicating that the second component 50 is attached to the console 10 via the intermediate component 20 and the first component 30 is not attached to the console 10 via the intermediate component 20) is provided.

Further, upon determining that a baseline signal is provided, the controller circuit 1370 is configured to provide feedback to the user through an output device such as a display prompting the user to attach the first component 30 and the second component 50 to the console 10. Further, the controller circuit 1370 is configured to provide feedback to the user to verify that the first component 30 and the second component 50 are securely attached to the console 10 via the intermediate component 20.

Further, upon determining that a first attachment state signal is provided, the controller circuit 1370 is configured to provide feedback to the user to attach the second component 50. Further, the controller circuit 1370 is configured to provide feedback to the user to verify that the second component 50 is securely attached to the console 10 via the intermediate component 20.

Further, upon determining that the third attachment state signal is provided, the controller circuit 1370 is configured to provide feedback to the user to attach the first component 30 to the console 10. Further, the controller circuit 1370 can be configured to provide feedback to the user to verify that the first component 30 is securely attached to the console 10 via the intermediate component 20.

In another example, the controller circuit 1370 is configured to control the first function module FM1 to generate the therapy signal only in response to the first attachment state signal or the second attachment state signal, and to control the second function module FM2 to provide irrigation, suction, or both only in response to the second attachment state signal or the third attachment state signal. That is, therapy signal is not generated if attachment of the interchangeable tip/blade module of the first component 30 to the console 10 via the intermediate component 20 is not confirmed. Further fluid irrigation, suction, or both is not provided if attachment of the second component 50 (including the fluid tube 2000) to the console 10 via the handpiece of the intermediate component 20 is not confirmed.

TWELFTH EMBODIMENT

In a twelfth embodiment, a method of providing a surgical system as described in one or more of the first to eleventh embodiments is provided.

In the method, a console including a controller and one or more function modules is provided. The one or more function modules are configured to be controlled to perform one or more predetermined functions. Further, the controller is configured to control the one or more function modules.

In the method, a first component configured to be directly or indirectly detachably attached to the console is provided.

In the method, a second component configured to be directly or indirectly detachably attached to one of the console and the first component is provided.

In the method, a target state detection circuit arranged to the console is provided. The target state detection circuit includes a detection signal generation circuit and a reference circuit. The detection signal generation circuit is configured to generate a detection signal. Further, the reference circuit is configured to provide a baseline signal based on the detection signal.

In the method, a first target state identification circuit arranged to the first component is provided. The first target state identification circuit is configured to be selectively electrically connected in a first attached state to the target state detection circuit. Further, in the first attached state, the target state detection circuit and the first target state identification circuit are configured to provide a first attachment state signal based on the detection signal.

In the method, a second target state identification circuit arranged to the second component is provided. The second target state identification circuit is configured to be selectively electrically connected in a second attached state to the target state detection circuit. Further, in the second attached state, the target state detection circuit and the second target state identification circuit are configured to provide a second attachment state signal based on the detection signal.

In the method, the target state detection circuit is enabled to output a feedback signal based on the baseline signal, the first attachment state signal, and the second attachment state signal.

In the method, the controller is enabled to control the one or more function modules based on the feedback signal.

While the invention has been particularly shown and described with respect to preferred embodiments thereof, it will be understood by those skilled in the art that the foregoing and other changes in form and details may be made therein without departing from the spirit and scope of the present invention.

The claimed invention is:

1. A surgical system comprising:
   a console comprising:
      a function module configured to be controlled to perform a predetermined function; and
      a controller configured to control the function module;
   a first component configured to be directly or indirectly detachably attached to the console;
   a second component configured to be directly or indirectly detachably attached to one of the console and the first component,
   a target state detection circuit arranged to the console, the target state detection circuit comprising:
      a detection signal generation circuit configured to generate a detection signal; and
      a reference circuit configured to provide a baseline signal based on the detection signal;
   a first target state identification circuit arranged to the first component,
      wherein the first target state identification circuit is configured to be selectively electrically connected in a first attached state to the target state detection circuit, and
      wherein in the first attached state, the target state detection circuit and the first target state identification circuit are configured to provide a first attachment state signal based on the detection signal; and
   a second target state identification circuit arranged to the second component, wherein the second target state identification circuit is configured to be selectively electrically connected in a second attached state to the target state detection circuit, and wherein in the second attached state, the target state detection circuit and the second target state identification circuit are configured to provide a second attachment state signal based on the detection signal, wherein the target state detection circuit is configured to output a feedback signal based on the baseline signal, the first attachment state signal, and the second attachment state signal, and wherein the controller is configured to control the function module based on the feedback signal.

2. The surgical system according to claim 1, wherein the target state detection circuit is arranged as an astable oscillator circuit.

3. The surgical system according to claim 1, wherein the target state detection circuit and one or more of the first target state identification circuit and the second target state identification circuit are arranged as an astable oscillator circuit.

4. The surgical system according to claim 1, wherein the target state detection circuit is arranged as a voltage sensor circuit.

5. The surgical system according to claim 1, wherein the target state detection circuit and one or more of the first target state identification circuit and the second target state identification circuit are arranged as a voltage sensor circuit.

6. The surgical system according to claim 1,
wherein the reference circuit comprises a reference capacitor or a reference resistor,
wherein the first target state identification circuit comprises one of:
a first target capacitor configured, in the first attached state, to be selectively electrically connected in parallel with the reference capacitor, and
a first target resistor configured, in the first attached state, to be selectively electrically connected in parallel with the reference resistor, and
wherein the second target state identification circuit comprises one of:
a second target capacitor configured, in the second attached state, to be selectively electrically connected in parallel with the reference capacitor, and
a second target resistor configured, in the second attached state, to be selectively electrically connected in parallel with the reference resistor.

7. The surgical system according to claim 6, wherein the one of the first target capacitor and the first target resistor of the first target state identification circuit is configured to be electrically connected in parallel with the corresponding reference capacitor and reference resistor by attaching the first component to the console.

8. The surgical system according to claim 6, wherein the first target state identification circuit further comprises a first target switch configured to be controlled to electrically connect the one of the first target capacitor and the first target resistor in parallel with the corresponding reference capacitor and reference resistor.

9. The surgical system according to claim 6, wherein the one of the second target capacitor and the second target resistor of the second target state identification circuit is configured to be electrically connected in parallel with the corresponding reference capacitor and reference resistor by attaching the second component to the one of the console and the first component.

10. The surgical system according to claim 6, wherein the second target state identification circuit further comprises a second target switch configured to be controlled to electrically connect the one of the second target capacitor and the second target resistor in parallel with the corresponding reference capacitor and reference resistor.

11. The surgical system according to claim 1, wherein in the absence of the first attachment state signal and the second attachment state signal, the baseline signal indicates that the first component and the second component are detached from the console.

12. The surgical system according to claim 1, wherein the first component is configured to be indirectly attached to the console via an intermediate component that is configured to be detachably attachable to the console.

13. The surgical system according to claim 1,
wherein the function module comprises a therapy signal generator configured to generate a therapy signal that is passed to one of the first component and the second component, and
wherein the controller is configured to control the therapy signal generator based on the feedback signal.

14. The surgical system according to claim 13,
wherein the console further comprises an electrical isolation device,
wherein the therapy signal generator is configured to generate the therapy signal as an AC signal, and to output the therapy signal to a pair of electrical leads,
wherein the feedback signal is referenced to one of the pair of electrical leads, and
wherein the target state detection circuit is configured to output the feedback signal through the electrical isolation device, and the electrical isolation device is configured to separate the feedback signal from the therapy signal and to provide the feedback signal to the controller.

15. A surgical system comprising:
a console comprising:
a function module configured to be controlled to perform a predetermined function; and
a controller configured to control the function module,
wherein the console is configured to be directly or indirectly detachably attached to a first component, and
wherein one of the console and the first component is configured to be directly or indirectly detachably attached to a second component; and
a target state detection circuit arranged to the console, the target state detection circuit comprising:
a device signal generation circuit configured to generate a detection signal; and
a reference circuit configured to provide a baseline signal based on the detection signal,
wherein the target state detection circuit is configured to be selectively electrically connected in a first attached state to a first target state identification circuit arranged to the first component,
wherein in the first attached state, the first target state identification circuit is configured to provide a first attachment state signal based on the detection signal,
wherein the target state detection circuit is configured to be selectively electrically connected in a second attached state to a second target state identification circuit arranged to the second component, wherein in the second attached state, the second target state identification circuit is configured to provide a second attachment state signal based on the detection signal, and wherein the target state detection circuit is configured to output a feedback signal based on the baseline signal, the first attachment state signal, and the second attachment state signal, and wherein the controller is configured to control the therapy signal generator based on the feedback signal.

16. A method comprising:

providing a console comprising:
- a function module configured to be controlled to perform a predetermined function; and
- a controller configured to control the function module;

providing a first component configured to be directly or indirectly detachably attached to the console;

providing a second component configured to be directly or indirectly detachably attached to one of the console and the first component, providing a target state detection circuit arranged to the console, the target state detection circuit comprising:
- a detection signal generation circuit configured to generate a detection signal; and
- a reference circuit configured to provide a baseline signal based on the detection signal;

providing a first target state identification circuit arranged to the first component,
wherein the first target state identification circuit is configured to be selectively electrically connected in a first attached state to the target state detection circuit, and
wherein in the first attached state, the target state detection circuit and the first target state identification circuit are configured to provide a first attachment state signal based on the detection signal;

providing a second target state identification circuit arranged to the second component,
wherein the second target state identification circuit is configured to be selectively electrically connected in a second attached state to the target state detection circuit, and
wherein in the second attached state, the target state detection circuit and the second target state identification circuit are configured to provide a second attachment state signal based on the detection signal;

enabling the target state detection circuit to output a feedback signal based on the baseline signal, the first attachment state signal, and the second attachment state signal; and enabling the controller to control the function module based on the feedback signal.

* * * * *